United States Patent
Webster et al.

(10) Patent No.: US 8,152,756 B2
(45) Date of Patent: Apr. 10, 2012

(54) ACTIVE CANNULA FOR BIO-SENSING AND SURGICAL INTERVENTION

(75) Inventors: Robert James Webster, Nashville, TN (US); Allison M. Okamura, Ruxton, MD (US); Noah J. Cowan, Baltimore, MD (US); Russell H. Taylor, Severna Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 467 days.

(21) Appl. No.: 12/084,979

(22) PCT Filed: Nov. 15, 2006

(86) PCT No.: PCT/US2006/044386
§ 371 (c)(1),
(2), (4) Date: Dec. 11, 2008

(87) PCT Pub. No.: WO2007/059233
PCT Pub. Date: May 24, 2007

(65) Prior Publication Data
US 2009/0171271 A1     Jul. 2, 2009

Related U.S. Application Data

(60) Provisional application No. 60/736,789, filed on Nov. 15, 2005, provisional application No. 60/849,788, filed on Oct. 6, 2006.

(51) Int. Cl.
*A61M 31/00*     (2006.01)

(52) U.S. Cl. .................................................... 604/95.01
(58) Field of Classification Search ............... 604/95.01, 604/532, 528; 600/585; 606/130, 114
See application file for complete search history.

(56) References Cited

U.S. PATENT DOCUMENTS

| | | | |
|---|---|---|---|
| 7,090,683 B2 * | 8/2006 | Brock et al. ................ 606/130 |
| 7,883,475 B2 | 2/2011 | Dupont et al. |
| 2002/0029013 A1 * | 3/2002 | Paskar ........................ 604/95.01 |
| 2002/0087048 A1 | 7/2002 | Brock et al. |
| 2002/0120178 A1 | 8/2002 | Tartaglia et al. |
| 2003/0109852 A1 | 6/2003 | Peterson et al. |
| 2004/0015151 A1 * | 1/2004 | Chambers .................... 604/532 |
| 2005/0154379 A1 | 7/2005 | McGowan, Sr. et al. |

FOREIGN PATENT DOCUMENTS

| | | |
|---|---|---|
| EP | 339 799 A2 | 11/1989 |
| EP | 1459692 A1 | 9/2004 |

* cited by examiner

*Primary Examiner* — Christopher D Koharski
(74) *Attorney, Agent, or Firm* — Venable LLP; Henry J. Daley

(57) ABSTRACT

Disclosed is a surgical needle, or active cannula, that is capable of following a complex path through cavities and tissue within a patient's anatomy. The needle has a plurality of overlapping flexible tubes, each of which has a pre-formed curvature and a pre-determined flexibility. Each of the plurality of flexible tubes is selected based on their respective pre-formed curvature and flexibility so that a given overlap configuration causes the combination of overlapping flexible tubes to form a predetermined shape that substantially matches a desired path through the anatomy. By individually controlling the translation and angular orientation of each of the flexible tubes, the surgical needle may be guided through the anatomy according to the desired path.

14 Claims, 7 Drawing Sheets

ACTIVE CANNULA FOR BIO-SENSING AND SURGICAL INTERVENTION

This application claims the benefit of U.S. Provisional Patent Application No. 60/736,789, titled ACTIVE CANNULAS FOR BIO-SENSING AND SURGICAL INTERVENTION, filed on Nov. 15, 2005, and U.S. Provisional Patent Application No. 60/849,788, titled METHOD FOR CONTROLLING SNAKE-LIKE ROBOTS FOR SURGICAL APPLICATIONS, filed on Oct. 6, 2006, which are hereby incorporated by reference for all purposes as if fully set forth herein.

BACKGROUND OF THE INVENTION

1. Field of the Invention

The present invention generally relates to surgical cannulas and bio-sensors for minimally invasive surgery. More particularly, the present invention relates to devices and techniques for guiding surgical instruments, injectable matter, diagnostic devices, and/or bio-sensors through complex trajectories.

2. Discussion of the Related Art

Minimally invasive surgical (MIS) techniques have revolutionized medicine in recent years by enabling surgical treatment without the massive trauma typically resulting from traditional open surgery. MIS techniques have enabled physicians to gain access to and perform interventions in anatomical regions previously unreachable under open surgical techniques. Further, MIS techniques have greatly reduced the trauma associated with surgery, thereby reducing surgery-related complications and expediting post-surgery recovery. Without viable MIS alternatives, surgery in confined spaces within the body (especially the head and neck) require large incisions and destructive dismantlement of healthy bone, skin, and muscle structure simply to enable tool access to the surgical site.

Related art MIS tools include rigid laparoscopic devices, which require a great deal of open space both inside and outside the body to perform dexterous motions in surgery. This requirement for open space generally precludes the use of laparoscopic devices in many types of surgery. Other related art MIS tools include flexible shape memory alloy devices, in which the shape of the device can be changed be applying heat to the shape memory alloy as the device is guided within a patient. One problem with such a device involves the unintended application of heat to the surrounding tissue. Another problem is that the thermal time constants of the shape memory alloy require considerable time (as long as several seconds) for appropriate heat to be applied and subsequently dissipated. The delays imposed by these thermal time constants limit the applicability of such MIS devices.

Other related art MIS devices include teleoperated surgical robots that typically have 5-10 mm diameter straight and rigid tools, which have a wire-actuated or push rod-actuated wrist. A problem with such related art surgical robots is that they are constrained to pivot at the body entry point and do not have the dexterity to maneuver through curved trajectories and around obstacles once within the body. By being constrained to pivoting at the body entry point, such surgical robots are generally unsuitable for complex surgical procedures, such as fetal surgery within the womb. In the case of fetal surgery, at least two pivot points are required: one at the mother's skin, and another at the wall of the uterus.

Surgical interventions involving the head and neck are particularly challenging, even with the advent of MIS techniques. For example, treatment of lesions at the base of the skull typically involve MIS devices being endoscopically inserted through the nose. Because related art MIS devices lack the dexterity to bend around and through small openings in the sinus cavities, many healthy tissue and bone structures, such as the nasal turbinates, must be removed to enable the MIS devices to access various surgical sites, including the base of the skull. Regarding nasal turbinates, their normal functions are to purify air and to aid in olefaction. Once removed for the purposes of gaining access to surgical sites, they cannot be reconstructed in such a way that their function is restored. Two exemplary surgical sites that cannot be reached using related art straight MIS devices include areas behind the carotid arteries (near the base of the eye) and the frontal sinus cavities, which involve reaching around a bone located directly behind the bridge of the nose.

Other examples of a surgical procedures in which related art MIS devices lack dexterity is lung surgery and throat surgery. Regarding lung surgery, a related art bronchoscope generally can only reach about ⅓ of the lung's interior. Currently, there are no low-risk methods of removing biopsy samples or directly treating cancer deeper within the lung. Further other related art methods of lung biopsy and treatment involve inserting needles, which incurs a substantial risk of complications, including lung deflation. Regarding throat surgery, lesions located deep within the throat are very difficult to access without large incisions. The large incisions are typically made to enable suturing. The throat itself as an avenue for suturing would mitigate the need for large incisions. However, related art MIS devices lack the dexterity to travel long distances through a laryngoscope, which typically has an 11 mm diameter.

Accordingly, what is needed is a surgical tool that has the dexterity to be maneuvered around anatomical features in order to gain access to otherwise unreachable surgical sites. Further, what is needed is a surgical device that can be guided through free space within a cavity, such as the sinuses, throat, and lungs, as well as through a tissue medium.

SUMMARY OF THE INVENTION

The present invention provides an active cannula for bio-sensing and surgical intervention that obviates one or more of the aforementioned problems due to the limitations of the related art.

Accordingly, one advantage of the present invention is that it provides a physician with better access to areas within the body that are typically unreachable.

Another advantage of the present invention is that it reduces the collateral trauma imposed on tissues in the course of gaining access to a tissue region of interest.

Still another advantage of the present invention is that it enables novel treatment methods.

Still another advantage of the present invention is that increases the accessibility of anatomical features to needles for the purposes of therapy and diagnostics.

Still another advantage of the present invention is that it provides better maneuverability for surgical instruments through both free space and tissue media.

Still another advantage of the present invention is that enhances the miniaturization of surgical cannulas.

Still another advantage of the present invention is that it enables safer guiding of surgical instruments in the presence of sensitive tissue.

Additional advantages of the invention will be set forth in the description that follows, and in part will be apparent from the description, or may be learned by practice of the invention. The advantages of the invention will be realized and attained by the structure pointed out in the written description and claims hereof as well as the appended drawings To achieve these and other advantages, the present invention involves a surgical cannula. The surgical cannula comprises a first flexible tube having a first pre-formed curvature; a second flexible tube having a second pre-formed curvature, wherein the second flexible tube is disposed within the first flexible tube; a first actuator coupled to the first flexible tube, wherein the first actuator controls a translation and a rotation of the first flexible tube; and a second actuator coupled to the second flexible tube, wherein the second actuator controls a rotation and translation of the second flexible tube independently of the translation and rotation of the first flexible tube.

In another aspect of the present invention, the aforementioned and other advantages are achieved by a computer readable medium encoded with software for guiding a surgical cannula, which comprises a program that receives a desired cannula path; a program that computes a configuration of a plurality of overlapping flexible tubes that substantially matches the desired cannula path; a program that computes a plurality of intermediate configurations corresponding to the desired cannula path; and a program that commands a plurality of actuators according to the plurality of intermediate configurations.

In another aspect of the present invention, the aforementioned and other advantages are achieved by a method for guiding a surgical cannula having a plurality of overlapping flexible tubes. The method comprises determining a desired needle path; selecting the plurality of flexible tubes, wherein each of the flexible tubes within the plurality has a pre-formed curvature and a flexibility; determining a final overlap configuration of the plurality of flexible tubes such that a resulting curvature of the overlap configuration substantially corresponds to the desired needle path; and determining a plurality of intermediate overlap configurations of the plurality of flexible tubes, wherein each of the intermediate configurations correspond to the desired needle path.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE ILLUSTRATED EMBODIMENTS

The present invention involves an active cannula, (also referred to as a surgical cannula) through which a surgical needle may be deployed. The active cannula may also be referred to as a snake-like surgical robot. The active cannula has a plurality of concentric flexible hollow tubes, wherein each tube has a predetermined flexibility and a pre-formed curvature. The tip of the active cannula is advanced by selectively translating and rotating each of the flexible tubes. Depending on the flexibility, preformed curvature, angular orientation, and translational position of each of the flexible tubes, the active cannula can be manipulated to take a planned complex shape that enables it to maneuver through free space (e.g., navigating through sinus passages or within bronchial airways) and/or through tissues of various resistances. The shape of the active cannula will also be affected by the resistance of the tissue medium in such a way that the resistance of the tissue medium may be taken advantage of in guiding the active cannula. Continuous actuation of the active cannula is derived from the elastic energy stored in each of the flexible tubes as each of the flexible tubes slide within each other during translation and rotation.

Further, the active cannula may take a complex shape as it is guided, either through free space or through a tissue medium, by "pushing against itself" via the interacting forces of the concentric flexible tubes. This contrasts with related art approaches of guiding needles by having them push against the tissue medium, wherein the tissue medium may be a soft tissue, or an anatomical feature such as an arterial wall.

Figure 1:
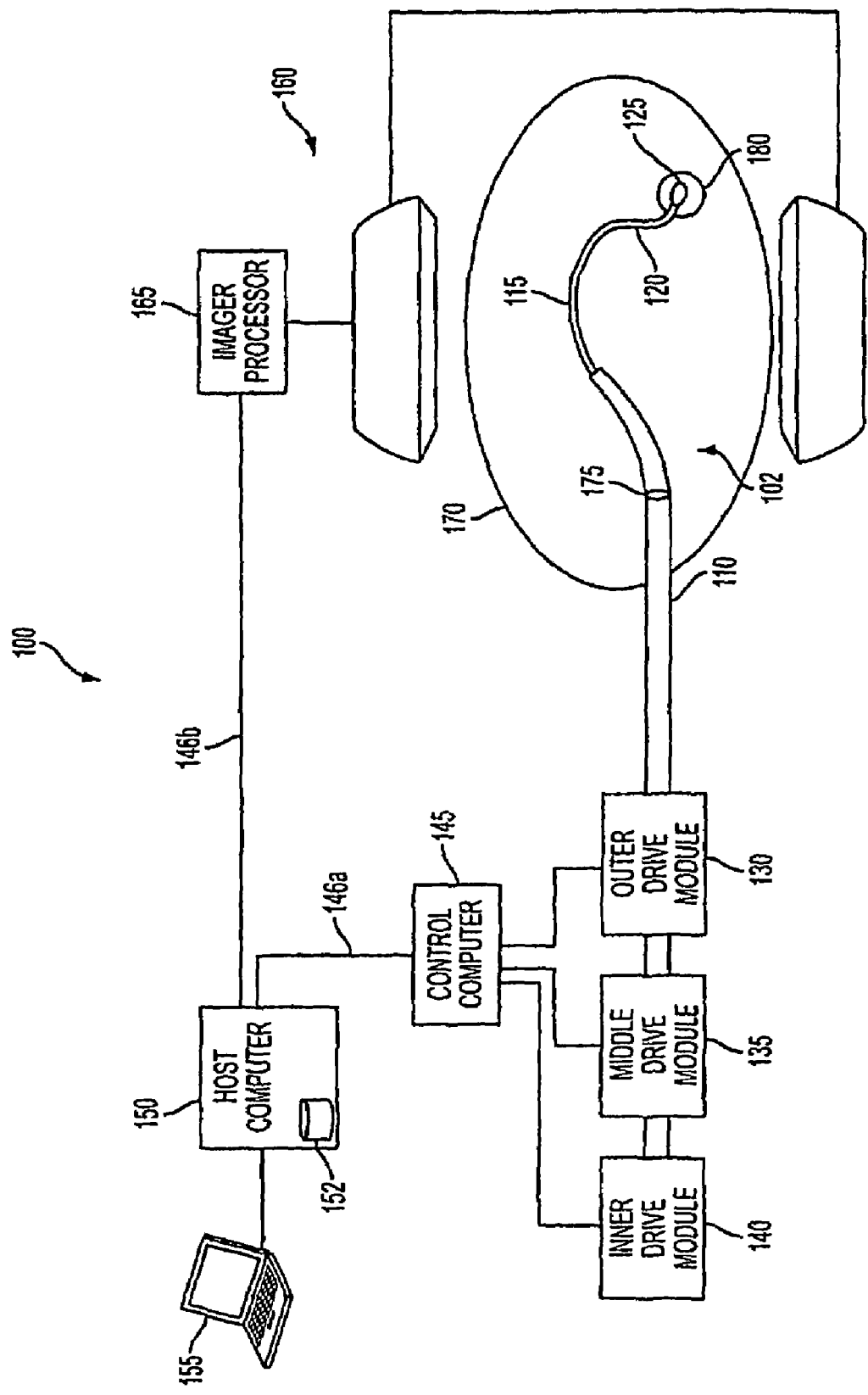
FIG. 1 illustrates an active cannula, and a system for controlling it, according to the present invention.

FIG. 1 illustrates an exemplary system 100 for controlling an active cannula according to the present invention. System 100 includes an active cannula 102 having an outer flexible tube 110, a middle flexible tube 115, and an inner flexible tube 120. Inner flexible tube 120 may have an end effector 125 at its end. System 100 further includes an inner drive module 140, which is coupled to inner flexible tube 120; a middle drive module 135, which is coupled to middle flexible tube 115; and an outer drive module 130, which is coupled to outer flexible tube 110. Inner drive module 140, middle drive module 135, and outer drive module 130 are connected to control computer 145.

Control computer 145 is connected to a host computer 150 over a control network connection 146a. Control network connection 146a may be a local area network (LAN) if host computer 150 and control computer 145 are co-located. Alternatively, host computer 150 and control computer 145 may be separated by great distances, in which case control network connection 146a may include the internet.

Host computer 150 includes a memory 152, which is encoded with software (hereinafter "the software") for implementing processes associated with the present invention. Host computer 150 is connected to a user interface 155. Host computer 150 may be a single computer or may include multiple computers that may be connected over a network, including the internet. Memory 152 may include a single memory device, such as a hard drive, or it may include multiple memory devices and databases that are distributed over multiple computers. One skilled in the art will readily appreciate that many such architectures for host computer 150, memory 152, and user interface 155, are possible and within the scope of the invention.

System 100 may further include a medical imaging system 160, which includes an image processor 165. Image processor 165 may be connected to host computer 150 over imaging network connection 146b, which may be the same type of network connection as control network connection 146a.

FIG. 1 illustrates active cannula 102 being deployed within a patient's anatomy 170, both of which are within the field of view of medical imaging system 160. Patient's anatomy 170 includes an entry point 175, where active cannula 102 enters the patient; and surgical site 180, which is the target site of interest within the patient at which the surgical intervention or diagnostic is to be performed.

Medical imaging system 160 may include one or more medical imaging modalities, such as fluoroscopy, MRI, ultrasound, and the like. The particular imaging modality of medical imaging system 160 may depend on the material used for active cannula 102 and the nature of the patient's anatomy 170 in which active cannula 102 is being deployed. Medical imaging system 160 may be of a type that provides 3-dimensional images with sufficient timeliness and sufficient frame rate to enable image-based feedback control of active cannula 102 by the software running on host computer 152.

Figure 2A:
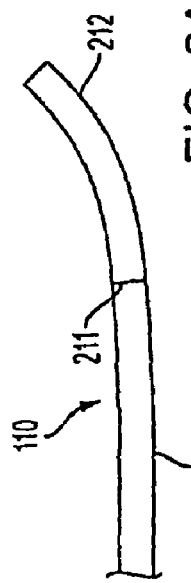
FIG. 2A illustrates an exemplary outer tube of the active cannula.

FIGS. 2A-2D illustrate active cannula 102 and its constituent flexible tubes. FIG. 2A illustrates an exemplary outer flexible tube 110. Outer flexible tube 110 may have an outer tube straight section 210, an outer tube curved section 212, and an outer tube transition point 211 defining the boundary between outer tube straight section 210 and outer tube curved section 212. Outer flexible tube 110 may have an inner diameter that is sufficiently wide to allow middle flexible tube 115 and inner flexible tube 120 to slide independently within the inner surface of outer flexible tube 110. The thickness of outer flexible tube 110 may be a function of the tube's desired flexibility, which is described herein further below. Accordingly, the thickness of outer flexible tube 110 may be tailored to provide a specified flexibility. The illustrated circular curvature of outer flexible tube 110 is exemplary, and many different curved shapes are possible, given the tube's material, its thickness, and the intended use of active cannula 102.

Outer flexible tube 110 may be made of a shape memory alloy, such as nitinol, although other materials may be used provided that they are suitable for surgical use and have a flexibility that can be predetermined by, for example, material properties or by specifying the thickness of the tube walls.

Figure 2B:
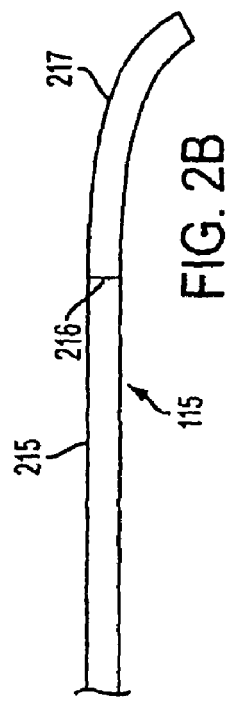
FIG. 2B illustrates an exemplary middle tube of the active cannula.

FIG. 2B illustrates an exemplary middle flexible tube 115. Middle flexible tube 115 may have a middle tube straight section 215, a middle tube curved section 217, and a middle tube transition point 216 defining the boundary between middle tube straight section 215 and middle tube curved section 217. Middle flexible tube 115 may have an inner diameter that is sufficiently wide to allow inner flexible tube 120 to slide within the inner surface of middle flexible tube 115. The thickness of middle flexible tube 115 may be a function of the tube's desired flexibility, which is described herein further below. Accordingly, the thickness of middle flexible tube 115 may be tailored to provide a specified flexibility. The illustrated curvature of middle flexible tube 115 is exemplary, and many different curvatures are possible, given the tube's material, its thickness, and the intended use of active cannula 102.

As in the case of outer flexible tube 110, middle flexible tube 115 may be made of a shape memory alloy, such as nitinol, although other materials may be used provided that they are suitable for surgical use and have a flexibility that can be predetermined by, for example, specifying a certain thickness for the tube. Further, middle flexible tube 115 may or may not be made of the same material as outer flexible tube 110, depending on the intended shape, thickness, and overall flexibility of active cannula 102.

Figure 2C:
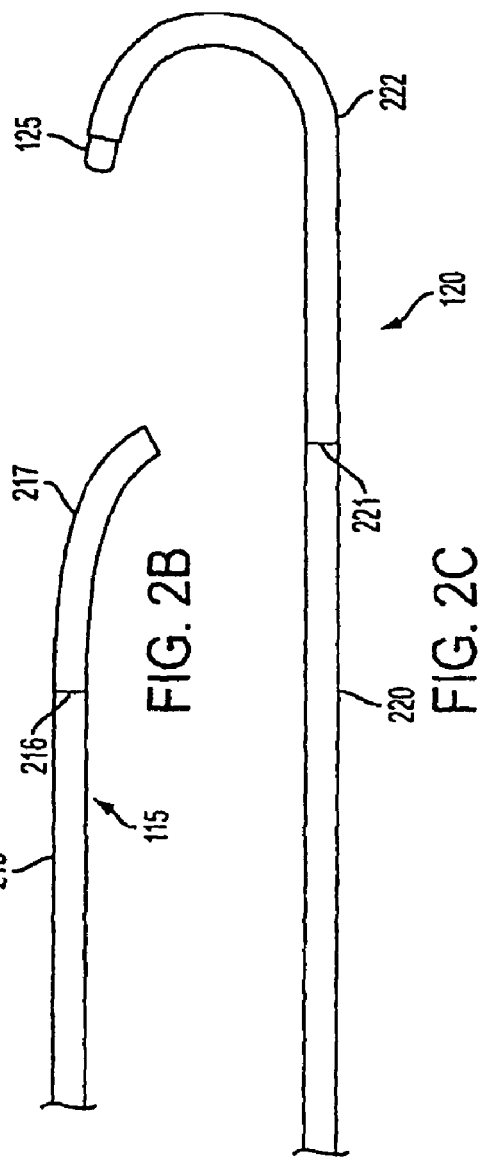
FIG. 2C illustrates an exemplary inner tube of the active cannula.

FIG. 2C illustrates an exemplary inner flexible tube 120. Inner flexible tube 120 may have an inner tube straight section 220, an inner tube curved section 222, and an inner tube transition point 221 defining the boundary between inner tube straight section 220 and inner tube curved section 222. Inner flexible tube 120 may have an inner diameter that is sufficiently wide to serve as a cannula for passing fluids, etc. Further, the inner diameter may be sufficiently wide to enable a cable, such as a wire, needle, elastic push-rod, or fiberoptic cable, to be carried to end effector 125. The thickness of inner flexible tube 120 may be a function of the tube's desired flexibility, which is described herein further below. Accordingly, the thickness of inner flexible tube 120 may be tailored to provide a specified flexibility. The illustrated curvature of inner flexible tube 120 is exemplary, and many different curvatures are possible, given the tube's material, its thickness, and the intended use of active cannula 102.

As in the case of outer flexible tube 110, inner flexible tube 120 may be made of a shape memory alloy, such as nitinol, although other materials may be used provided that they are suitable for surgical use and have a flexibility that can be predetermined by, for example, specifying a certain thickness for the tube. Further, inner flexible tube 120 may or may not be made of the same material as outer flexible tube 110 and middle flexible tube 115.

End effector 125 may be one of many devices suitable for the intended surgical intervention. For example, end effector 125 may be a thermal ablation probe, a fiber-optic camera, a tip for injecting radioactive seeds, a needle for performing a biopsy, and the like. Further, end effector 125 may be used for acquiring tissue or fluid samples for external analysis. Still further, end effector 125 may be a bio-sensor to be deployed within a site of interest. Such bio-sensors may include stereotactic positioners (e.g., magnetic trackers), molecular sensors, electrical impedance sensors, contactless mechanical impedance sensors, optical luminescent sensors, and the like. It will be readily apparent to one skilled in the art that end effector 125 may take many forms and perform many different functions, all of which are within the scope of the invention.

Figure 2D:
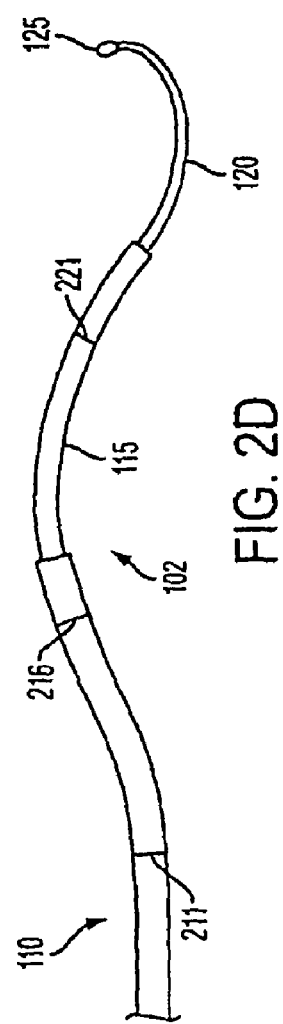
FIG. 2D illustrates an exemplary active cannula that includes the three tubes illustrated in FIGS. 2A-C.

FIG. 2D illustrates active cannula 102, including each of the tubes illustrated in FIGS. 2A-D. Inner flexible tube 120 is illustrated as inserted into middle flexible tube 115, and the combination of inner flexible tube 120 and middle flexible tube 115 are inserted within outer flexible tube 110.

Figure 3:
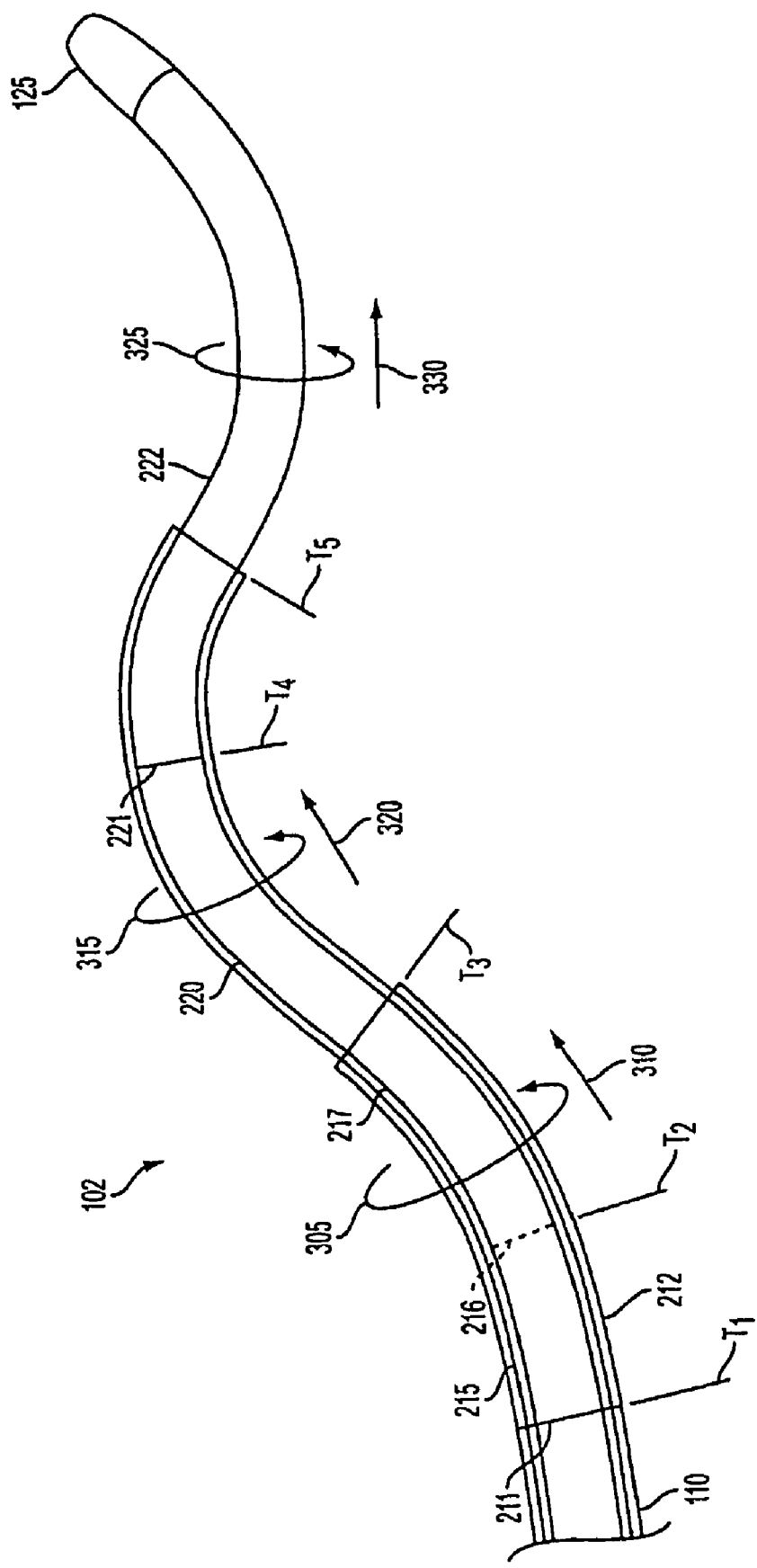
FIG. 3; further illustrates the active cannula of FIG. 2B, including degrees of freedom of each tube.

FIG. 3 illustrates active cannula 102, including inner flexible tube 120, middle flexible tube 115, and outer flexible tube 110. As illustrated, each flexible tube has two degrees of freedom: one around an axial rotational axis, and another along a linear translational axis. For example, outer flexible tube 110 has an outer rotational degree of freedom 305 and an outer translation degree of freedom 310. Outer rotational degree of freedom 305 and outer translational degree of freedom 310 apply to outer flexible tube 110 independently of the other tubes. Middle flexible tube 115 has a middle rotational degree of freedom 315 and a middle translation degree of freedom 320, both of which apply only to middle flexible tube 115 independently of the other tubes. Inner flexible tube 120 has an inner rotational degree of freedom 325 and an inner translation degree of freedom 330, both of which apply to inner flexible tube 120 independently of the other tubes.

Referring again to FIG. 3, active cannula 102 has a plurality of overlap transition points $T_1$-$T_5$. Each overlap transition point $T_1$-$T_5$ defines a boundary of a region in which the each of outer flexible tube 110, middle flexible tube 115, and inner flexible tube 120 (or some subset of the three) have a substantially constant degree of curvature, or lack of curvature. For example, the region between overlap transition points $T_1$ and $T_2$ includes outer tube curved section 212, middle tube straight section 215, and inner tube straight section 220. Overlap transition point $T_2$ is coincident with middle tube transition point 216. Accordingly, the region between $T_2$ and $T_3$ includes outer tube curved section 212, middle tube curved section 217, and inner tube straight section 220.

Each region bounded by at least one of overlap transition points $T_1$-$T_5$ has a curvature that is a function of the curvatures and flexibilities of each of outer flexible tube 110, middle flexible tube 115, and outer flexible tube 120, as well as the resistance of the surrounding tissue medium. One will note that some regions have only middle flexible tube 115 and inner flexible tube 120. In this case, the curvature of that region is a function of the curvature of those two tubes within the region. In the simplest case, the curvature of the region from $T_5$ to end effector 125 is a function of the curvature of inner flexible tube 120 and the resistance of the surrounding tissue medium.

Figure 4A:
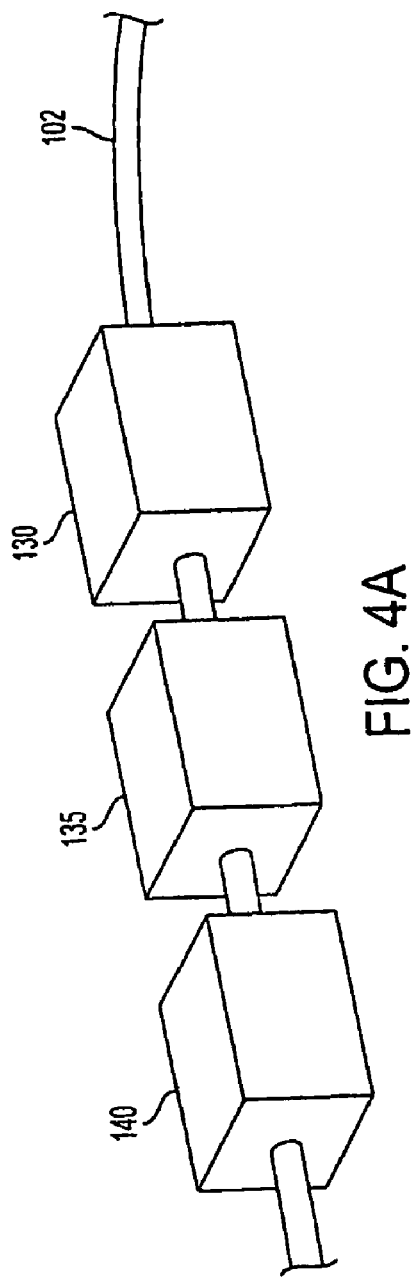
FIG. 4A illustrates a set of two-axis actuators according to the present invention.

FIG. 4A illustrates a set of two-axis actuators according to the present invention. The two-axis actuators include outer drive module 130, which is coupled to outer flexible tube 110; middle drive module 135, which is coupled to middle flexible tube 115; and inner drive module 140, which is coupled to inner flexible tube 120. Each of these drive modules independently drive their respective flexible tube. For example, outer drive module 130 drives outer flexible tube 110 about outer rotational degree of freedom 305 and along outer translational degree of freedom 310. Middle drive module 135 drives middle flexible tube 115 about middle rotational degree of freedom 315 and along middle translational degree of freedom 320. And inner drive module 140 drives inner flexible tube 120 about inner rotational degree of freedom 325 and inner translational degree of freedom 330.

Figure 4B:
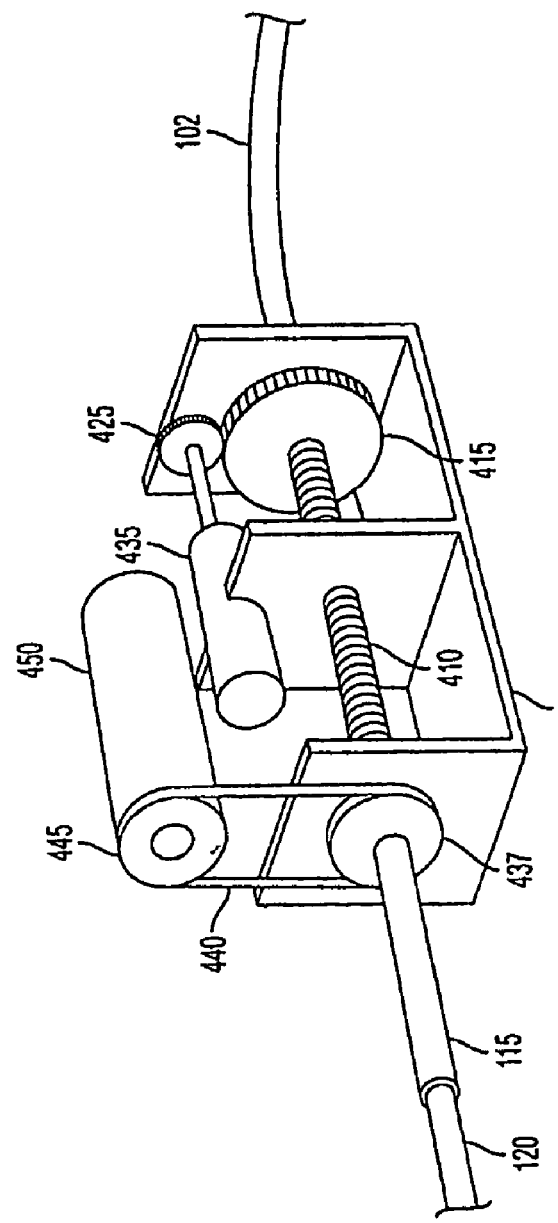
FIG. 4B illustrates an exemplary mechanism for a two-axis actuator.

FIG. 4B illustrates an exemplary two-axis actuator 405 according to the present invention. Two-axis actuator 405 may be used for any of outer drive module 130, middle drive module 135, and inner drive module 140. Two-axis actuator 405 includes a lead screw 410, which may be rigidly attached to a flexible tube (outer flexible tube 110 is illustrated as an example); a nut 415 that is threaded onto lead screw 410; and a linear translation motor 435, which is coupled to nut 415 via translation gear 425. Two-axis actuator 405 further includes a belt drive 440, which is coupled to lead screw 410 via sprocket 437. Belt drive 440 is also coupled to rotation motor 450 via rotation gear 445. Two axis actuator 405 may also include translational and rotational encoders (not shown) that respectively provide linear translation position and angular orientation signals to control computer 145.

Two-axis actuator 405 may operate as follows. In the case of linear translation, linear translation motor 430 receives commands from control computer 145 to translate its flexible tube according to a particular translation distance. In response, linear translation motor 430 rotates translation gear 425, which engages nut 415. The subsequent rotation of nut 425 engages lead screw 410, which translates the flexible tube.

In the case of rotation, rotation motor 450 receives commands from control computer 145 to rotate according to a particular rotation angle. In response, rotation motor 450 rotates rotation gear 445, which engages belt drive 440. Belt drive 440 engages sprocket 437, which in turn rotates lead screw 410. Note, this rotation of lead screw 410 causes a translation of lead screw 410 due to the presence of nut 415. Accordingly, to prevent a parasitic translation, linear translation motor 430 compensates by rotating nut 415 in the opposite direction. As such, pure rotation of the flexible tube may require coordinated motion by rotation motor 450 and linear translation motor 430.

As illustrated in FIG. 4B, lead screw 410 may be hollow. In this case, if two-axis actuator 405 serves as outer drive module 130, then outer flexible tube 110 is coupled to lead screw 410, and middle flexible tube 115 and inner flexible tube 120 may independently translate and rotate within the hollow portion of lead screw 410. In this way, outer flexible tube 110, middle flexible tube 115, and inner flexible tube 120 may be translated and rotated independently.

Figure 5:
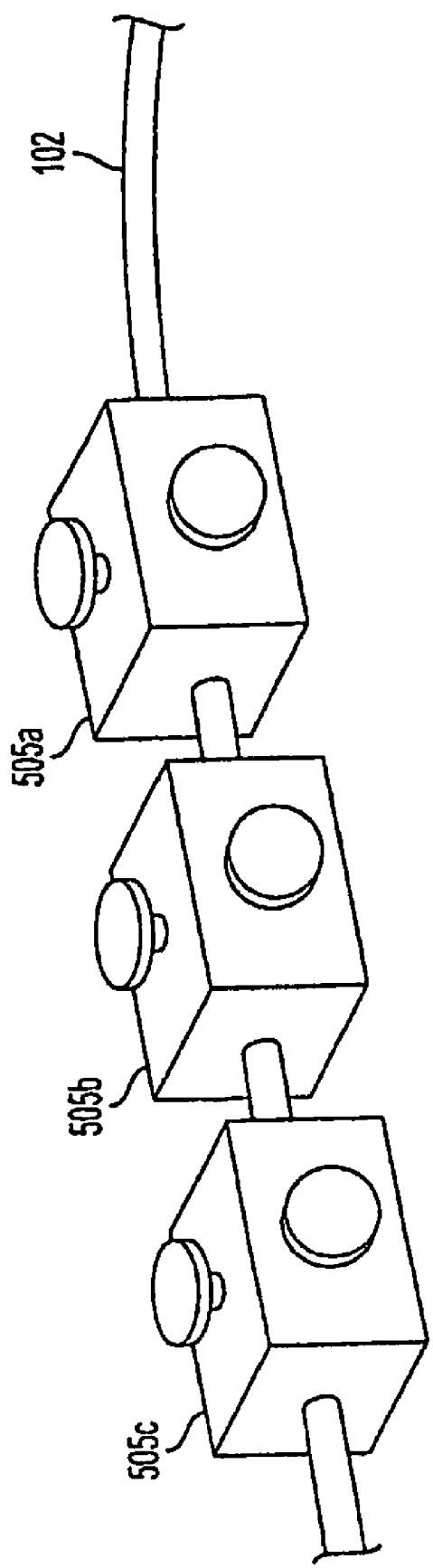
FIG. 5 illustrates a set of manual actuators.

FIG. 5 illustrates a set of manual two-axis actuators 505a-c. Here, manual two-axis actuator 505a may drive outer flexible tube 110 in place of outer drive module 130; manual two-axis actuator 505b may drive middle flexible tube 115 in place of middle drive module 135; and manual two axis actuator 505c may drive inner flexible tube 120 in place of inner drive module 140. Each of manual two axis actuators 505a-c may include translational and rotational encoders, which provide linear position and angular orientation signals to control computer 145.

Variations to the two-axis drive modules are possible. For example, two-axis actuator 405 may include manual controls, such as knobs, which respectively override linear translation motor 430 and rotational motor 450. Further, system 100 may include a combination of motor-driven and manual actuators. Further, two-axis actuator 405 is exemplary. As such, there may be other ways of achieving linear translation and rotation of each of the flexible tubes apart from the ways shown here. One skilled in the art will readily appreciate that many such variations are possible and within the scope of the invention.

Figure 6:
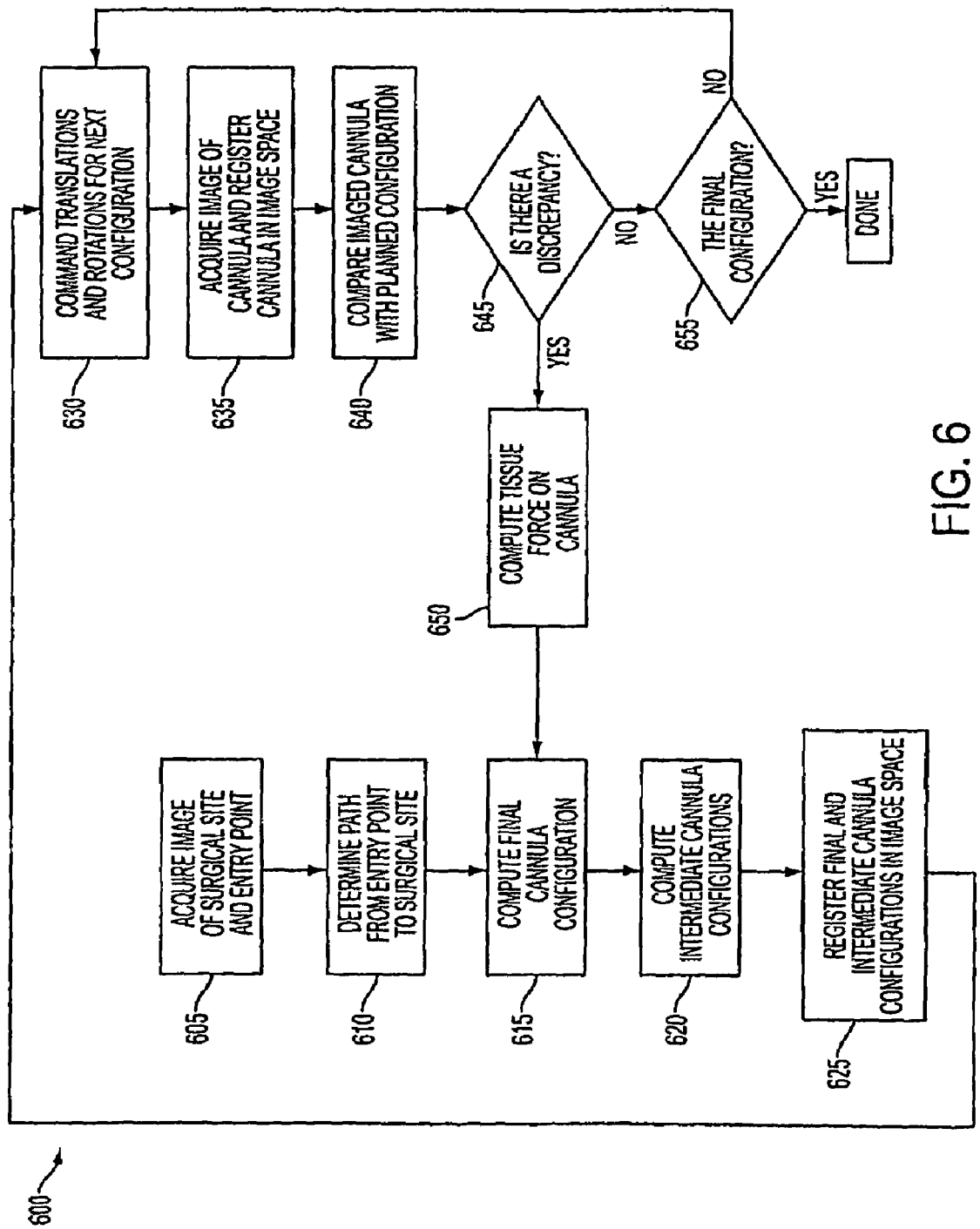
FIG. 6 is an exemplary process for controlling an active cannula.

FIG. 6 illustrates an exemplary process 600 for controlling an active cannula associated with the present invention. All or part of process 600 may be performed by the software stored on memory 152 and executed on host computer 150 and/or control computer 145 and/or imager processor 165. Process 600 may be divided into two sub-processes: path planning (steps 605-625) and path plan execution (steps 630-655).

In step 605, medical imaging system 160 acquires an image of patient's anatomy 170. Medical imaging system 160 may be configured to have a field of view than encompasses entry point 175 and the surgical site 180. Depending on its imaging modality (e.g. MRI, ultrasound, etc.), medical imaging system 160 may acquire a 3-D image of patient's anatomy, whereby each pixel or voxel of the image is registered to an image coordinate frame. Imager processor 165 may provide the image, as well as image registration information, to host computer 150 over imaging network connection 146b.

In step 610, the physician determines a desired path from entry point 175 to surgical site 180. In doing so, the physician may identify a path through which active cannula 102 will travel, along with an error boundary around the path. Depending on the location of surgical site 180, and the presence of intervening tissue or organs, the path may involve a complex path having variable error boundaries.

The physician may use user interface 155 to define the path and its error boundaries. In doing so, the physician may use a cursor to tag points within the registered image acquired in step 605. The software identifies the location of these selected points in the registered image and stores these locations in memory 152.

In step 615, the software computes a final configuration of active cannula 102 that will achieve the path selected in step 610. In doing so, the software may determine the translational position and rotational orientation of each of outer flexible tube 110, middle flexible tube 115, and inner flexible tube 120, that will make active cannula 102 conform to the path.

In computing a final configuration that conforms to the path, the software divides active cannula 102 into a set of regions defined by overlap transition points $T_1$-$T_5$. In doing so, the software may select an initial set of translational positions and rotational orientations for each of outer flexible tube 110, middle flexible tube 115. The locations of overlap transition points $T_1$-$T_5$ depends on the overlap of the three flexible tubes. Then for each region bounded by overlap transition points $T_1$-$T_5$, the software computes the instantaneous equilibrium curvature (in x and y components) in that region according to the following relation:

$$\kappa_x = \frac{\sum_{i=1}^{n} E_i I_i \cos(\theta_i - \phi)\kappa_i}{\sum_{i=1}^{n} E_i I_i}$$

and $$\kappa_y = \frac{\sum_{i=1}^{n} E_i I_i \sin(\theta_i - \phi)\kappa_i}{\sum_{i=1}^{n} E_i I_i}$$

where n is the number of flexible tubes (n=3 in this example); $\kappa_i$ is the instantaneous curvature of the $i_{th}$ flexible tube in that region; $E_i$ is the Modulus of Elasticity (Young's Modulus) of the material in the $i_{th}$ flexible tube; $I_i$ is the cross sectional moment of inertia of the $i_{th}$ flexible tube; $\theta_i$ is the angular orientation of the $i_{th}$ flexible tube at the closest overlap transition point T in the direction toward the actuators; and $\phi$ is the equilibrium angle of combined flexible tubes given their individual angular orientations, wherein $\phi$ is determined at the base of the region. In other words, for example, for a region bounded by overlap transition points $T_3$ and $T_4$, $\phi$ is pertains to the equilibrium angle at $T_3$.

Of these terms, $\kappa_i$, $E_i$, and $I_i$ are known. The remaining terms are solved for by (1) computing the torsional energy in the straight sections between the actuators and the first transition point and the bending energy (as a function of flexible tube orientations) stored in active cannula, and (2) solving for the shape that provides the minimum energy. In doing so, the software computes the torsional energy stored in straight sections 210, 215, and 220 of outer flexible tube 110, middle flexible tube 115, and inner flexible tube 120, respectively; and the software computes the bending energy stored in curved sections 212, 217, and 222 of outer flexible tube 110, middle flexible tube 115, and inner flexible tube 120, respectively. The software does this by computing the combined stored energy according to the following relation:

$$E(q) = \sum_{i=1}^{n} \frac{G_i J_i}{L_i}(\alpha_i - \theta_{i,1})^2 +$$

$$\sum_{j=1}^{m}\sum_{i=1}^{n} \frac{E_i I_i l_i}{2}((\kappa_x - \kappa_i \cos(\theta_{i,j} - \phi_j))^2 + (\kappa_i \sin(\theta_{i,j} - \phi_j))^2)$$

where $\alpha_i$ is the angle input at inner drive module 140, middle drive module 135, and outer drive module 130; $\theta_{i,j}$ is the angle of the $i_{th}$ flexible tube at the $j_{th}$ transition point $T_j$; $\phi_1, \phi_2, \ldots \phi_m$ are the equilibrium planes of each of the m regions of overlap between overlap transition points T; and $q=(\theta_{1,1}, \theta_{1,2}, \ldots \theta_{1,n}, \phi_1, \phi_2, \ldots, \phi_m)$. Solving for the minimum value of E(q) yields the rotational orientations $\theta_{1,1}, \theta_{1,2}, \ldots, \theta_{1,n}$ at $T_1$, and the equilibrium planes $\phi_1, \phi_2, \ldots, \phi_m$ of each region of overlap between transition points T. These values can also be used in the equations for $\kappa_x$ and $\kappa_y$ above to compute the curvatures in each overlap region between transition points T of active cannula 102.

Figure 7:
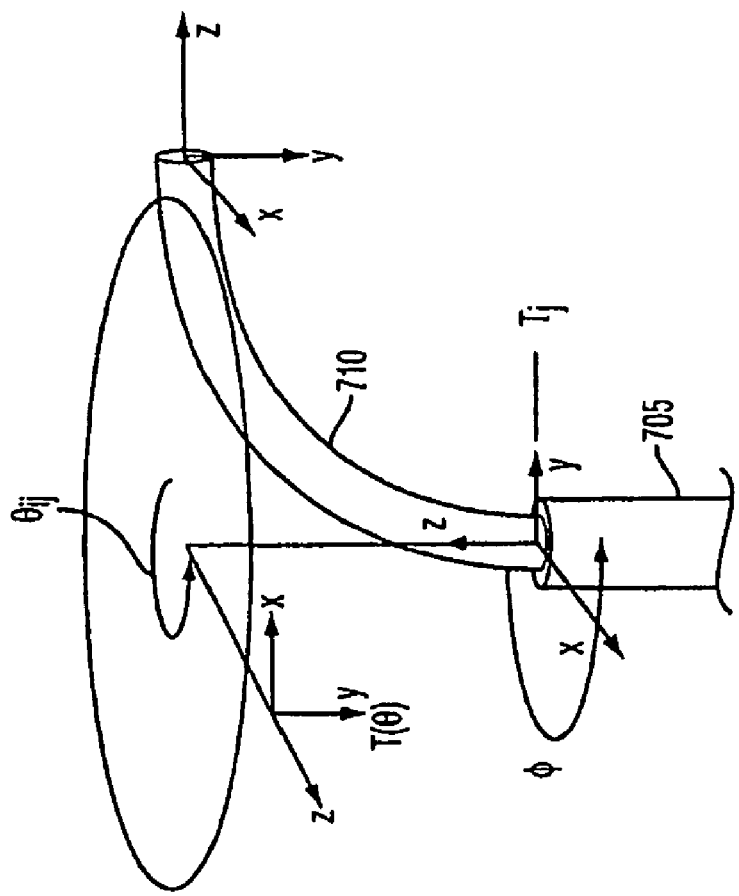
FIG. 7 illustrates a kinematic frame for controlling a tube.

FIG. 7 illustrates a kinematic frame for controlling a flexible tube. As illustrated, $\phi$ refers to the equilibrium angle of flexible tube 710 at an overlap transition point $T_j$, and $\alpha$ refers to the input rotation angle imparted by the rotational motor of two-axis actuator 405.

Further to step 615, the software may select different tubes from among an inventory of tubes for outer flexible tube 110, middle flexible tube 115, and inner flexible tube 120. In this case, a plurality of each flexible tube types may be available, and their characteristics (length of straight section, length of curved section, radius of curvature of the curved section, flexibility, etc.) may be stored in memory 152. As such, the software may repeat the above computation within step 610 described above, wherein each iteration uses a different available tube. In this manner, the software can determine two things: first, whether the path determined by the physician can be replicated by active cannula 102; and second, what combination of tubes will achieve that path. Further, the above relations are not limited to three flexible tubes. Accordingly, the software may select varying combinations of tubes, including the number of flexible tubes to be used, in order to achieve the path determined by the physician. One skilled in the art will understand how to implement the above equations for more than three flexible tubes.

In step 620, the software computes a plurality of configurations for active cannula 102 that will enable active cannula to gradually achieve the final configuration computed in step 615, while not having the active cannula stray beyond the path and error boundaries determined by the physician. In doing so, the software may compute a series of intermediate configurations, and compute a set of linear translations and rotations that will achieve each intermediate configuration. The software may iteratively perform computations substantially similar to that performed in step 615 above, with the resulting configuration for each computed intermediate configuration being the initial configuration for the next computed intermediate configuration.

Further to step 620, the software may compute a sequence of rotation commands for rotation motors 450 and linear translation commands for linear translation motors 430, of each outer drive module 130, the middle drive module 135, and the inner drive module 140, in order to achieve each intermediate configuration in sequence.

In step 625, the software registers the final and intermediate configurations for active cannula, as respectively computed in steps 615 and 620, in the coordinate frame of medical imaging system 160. In doing so, the software may retrieve the registered image acquired in step 605, in which the physician had designated a path in step 610, and register the final and intermediate configurations of active cannula 102. The result of this may be a set of curves, one per intermediate configuration and one for the final configuration, wherein each set of curves corresponds to the regions of active cannula 102 between a overlap transition points $T_1$-$T_5$. The software may do this by starting at an origin point for the active cannula (registered in image space), proceeding through entry point 175, and concluding at surgical site 180 (or at end effector 125 for active cannula 102 in an intermediate configuration). The software stores these sets of curves in memory 152.

This completes the exemplary path planning subprocess of process 600. The path planning sub-process may be performed in the operating room, immediately before performing surgery. Alternatively, the path planning sub-process may be done pre-operatively and in a different setting than the operating room. In the latter case, the image acquired in step 605 may be out of date, because the patient will have moved between the path planning sub-process and the execution sub-process. In this case, a new registered image will have to be acquired by medical imaging system 160 as a precursor to the execution sub-process, and the newly-acquired image will have to be registered to the earlier registered image having the registered configurations (curves) of active cannula 102 computed in step 625. Further information regarding robotic path planning can be found in *Planning Algorithms*, Steven M. LaValle, Cambridge University Press (2006), (ISBN-10: 0521862051| ISBN-13: 9780521862059), which is hereby incorporated by reference as if fully disclosed herein.

At the outset of the execution sub-process, the patient is prepared for surgery and patient's anatomy 170 is placed within the field of view of medical imaging system 160, as illustrated in FIG. 1. Active cannula 102 is placed in the vicinity of entry point 175, and outer drive module 130, middle drive module 135, and inner drive module 140 are connected to active cannula 102. Control computer 145 is connected to the three drive modules 130, 135, and 140, and communications is established between control computer 145 and host computer 150 over control network connection 146a.

In step 630, the first step of the execution sub-process, the physician (via user interface 155) issues a command to the software to move active cannula 102 to the first intermediate configuration computed in step 630 (in the path planning sub-process). In doing so, the software, which may be running on host computer 150 and/or control computer 145, issues appropriate commands to the translational motors 430 and the rotational motors 450 of each of outer drive module 130, middle drive module 135, and inner drive module 140, to achieve the first intermediate configuration computed in step 620.

In step 635, medical imaging system 160 acquires an image of active cannula 102 within patient's anatomy 170. In doing so, imager processor 165 may segment and register active cannula 102 in the image coordinate frame. Imager processor 165 may employ one or more segmentation algorithms that are known to the art. Imager processor 165 may transmit the registration information and the image to host computer 150 over imaging network connection 136b. The software may receive the registration information and the image of active cannula 102 within patient's anatomy 107 and present the information and image to the physician via user interface 155.

In step 640, the software compares the registered image of cannula 102 with the intermediate configuration computed in step 620. In doing so, the software may employ one or more of a number of image processing algorithms for comparing the two images. Further, the software may compare the coordinates of the segmented and registered active cannula 102 with the computed coordinates of the given intermediate configuration and compute a path error, or differential displacement, based on this comparison.

In step 645, the software determines if there is a discrepancy between the segmented and registered active cannula 102 with the given intermediate configuration. If there is no discrepancy, process 600 proceeds through the "NO" branch from step 645 to step 655.

In step 655, the software determines if the given intermediate configuration is the final configuration computed in step 615. If it is, process 600 may proceed through the "YES" branch of step 655 to completion. If it is not the final configuration, then process 600 may proceed through the "NO" branch of step 655 to repeat steps 630-645 with the next intermediate configuration (or the final configuration).

Returning to step 645, if there is a discrepancy between the segmented and registered active cannula 102 with the given intermediate configuration, process 600 may proceed through the "YES" branch of step 645 to step 650.

In step 650, the software computes the force and torque exerted on active cannula 102 as it was pushed through patient's anatomy 170 in step 630. The software may compute the force and the torque according to the following relations:

$$\begin{bmatrix} f_x \\ f_y \\ f_z \\ \tau_x \\ \tau_y \\ \tau_z \end{bmatrix} = [K] \begin{bmatrix} disp_x \\ disp_y \\ disp_z \\ rot_x \\ rot_y \\ rot_z \end{bmatrix}$$

where $f_{x,y,z}$ are components of the force imparted by the tissue medium on active cannula 102 at a given region between two overlap transition points $T_i$ and $T_{i+1}$i; $\tau_{x,y,z}$ are the torques imparted on active cannula 102 by the tissue medium on active cannula 102 at the same region; $disp_{x,y,z}$ are translational components of the differential displacement of active cannula 102 computed in step 640; $rot_{x,y,z}$ are the rotational components of the differential displacement of active cannula 102 computed in step 640; and K is a compliance matrix, which is a 6×6 matrix corresponding to the force and torque compliance of active cannula 102 for the given region between two overlap transition points $T_i$ and $T_{i+1}$.

Compliance matrix K may be predetermined in a calibration procedure in which active cannula 102 is translated and rotated in one or more phantoms having known resistance properties. In addition, if compliance matrix K is known, then active cannula 102 may be used as a force sensor. In this case, a physician may plan a path for active cannula (using all or part of exemplary process 600) so that end effector 125 may come in contact with a tissue region of interest. Once end effector 125 comes in contact with the tissue region of interest, the values for $f_{x,y,z}$ and $\tau_{x,y,z}$ computed in step 650 may respectively correspond to the force and torque imparted on end effector 125 by the tissue region of interest. Accordingly, active cannula 102 may be used as a force sensor.

Figure 8:
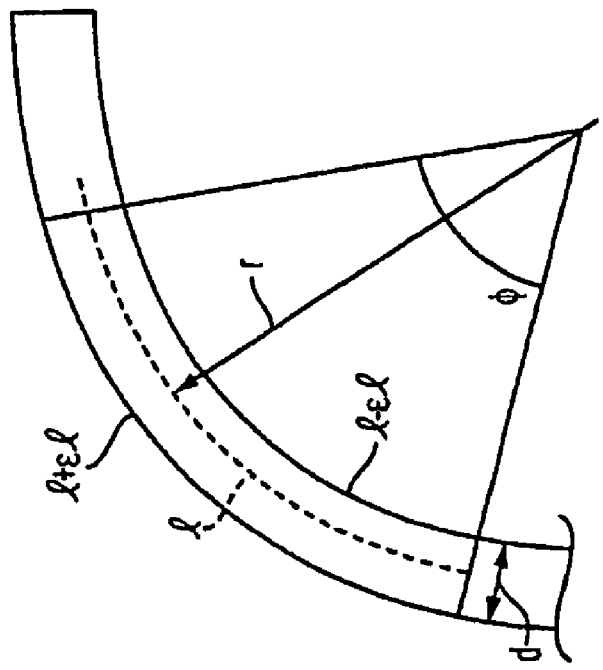
FIG. 8 illustrates how strain relates to the side lengths and curvature of a tube.

FIG. 8 illustrates how strain relates to the side lengths of a flexible tube, which may be any of outer flexible tube 110, middle flexible tube 115, and inner flexible tube 120. The software, in computing the final and intermediate configurations in steps 615 and 620, may determine the maximum degree of curvature, or minimum radius of curvature, beyond which a given flexible tube will suffer plastic deformation. Plastic deformation refers to the degree of bending of a shape memory material such that the material will no longer return to its original shape. This may correspond to a limit of permissible curvature of a flexible tube. The software may compute the maximum degree of curvature according to the following relation:

$$\kappa = \frac{2\varepsilon}{d(1+\varepsilon)}$$

where d is the diameter of the flexible tube, and $\varepsilon$ is the maximum recoverable strain for the flexible tube's material. For nitinol, $\varepsilon$ may range from 0.08 to 0.1. As can be inferred from the above relation, the thinner the flexible tube, the greater the maximum degree of curvature (or the lesser the minimum radius of curvature). Accordingly, depending on the path determined by the physician in step 610, a thinner flexible tube may be desired. The software may assist the physician in selecting a preferred thickness of flexible tube depending on the path determined in step 610.

Variations to active cannula 102, system 100, and process 600, are possible and within the scope of the invention. For example, some or all of the flexible tubes in active cannula 102 may have substantially the same degree of flexibility, or they may each have different degrees of flexibility. If all of the flexible tubes have a similar flexibility, it may make active cannula 102 more agile and easier to guide through complex paths. Alternatively, outer flexible tube 110 may be stiffer than middle flexible tube 115, which may be in turn stiffer than inner flexible tube 120. In the latter case, active cannula 102 may be less agile than in the former case (in which all the flexible tubes have the same flexibility). However, in the latter case, the path of active cannula 102 may be easier to compute, and it may better enable manual operation, for example, by using manual two-axis actuators 505 illustrated in FIG. 5.

In another variation, any of the flexible tubes may have non-circular inner and/or outer shapes. Such variations to a flexible tube's cross section may provide differing flexibility as a function of bend angle. Further, a flexible tube may have different shaped regions along its length, whereby each region may have a different cross sectional shape.

Any of the flexible tubes within active cannula 102 may have only a curved portion or a straight portion. Further, any of the flexible tubes may have multiple segments, each with a different degree of curvature (including no curvature). This may allow active cannula 102 to take more complex shapes. For example, any of the flexible tubes may have sequences of three-dimensional curves and straight regions. Also, any of the flexible tubes may have a segment having an complex shape, such as a helical shape, an elliptical shape, a parabolic shape, a variable curvature in three dimensions, and the like. In any of these cases, multiple transition points (like inner tube transition point 221, middle transition point 216, and outer tube transition point 211) may be defined that mark changes in radius of curvature of the particular flexible tube. Accordingly, discrete gradations of curvature may be segregated for the purposes of defining overlap regions, as part of computing cannula final and intermediate configurations in steps 615 and 620.

In another variation, one or more of the flexible tubes may be designed to have a variable stiffness according to the direction in which the flexible tube is bent. For example, one or more of the flexible tubes may have scores or grooves on the inner or outer surface of the flexible tube.

In another variation, one or more of the flexible tubes may include fiducials, which may be embedded within the tube material, and which may be designed to be visible to medical imaging system 160. For example, if medical imaging system 160 is an optical camera, embedded fiducials may take the form of colored stripes or bands of light and dark color. Further, if medical imaging system is a C-arm fluoroscope, embedded fiducials may include wire structures implanted within the tube material. One skilled in the art will readily appreciate that many such variations are possible and within the scope of the invention.

If nitinol is used for any of the flexible tubes described above, then system 100 may include one or more heater elements, which may run along one or more of flexible tubes 110, 115, and 120. According to this variation, heat can be applied to change the shape of a given flexible tube. One skilled in the art will understand how to integrate a heater element into active cannula 102 and system 100 and that such a variation is within the scope of the invention.

In addition to lung and throat surgery, as mentioned above, the present invention may be used in other surgical procedures, in which the dexterity afforded by active cannula 102 and system 100 may be advantageous. Such surgical procedures include Radiofrequency Ablation. In Radiofrequency Ablation, an electrode is placed at a surgical site, and then a painless radiofrequency energy is transmitted to heat the tissue surrounding the electrode. This procedure may be used to kill cells as part of a treatment for tumors of the liver, kidney, and lung. Active cannula 102 and system 100 may be employed to deploy the electrode.

Another possible surgical application involves surgical interventions on the posterior side of the retina. One such surgical intervention may include cannulation of the retina to treat clotting, which is one of the leading causes of blindness.

Another possible surgical application involves transgastric surgery, in which tools enter the stomach via the mouth, then exit the stomach into the abdominal cavity. The dexterity of active cannula 102, and its ability to be guided through free space as well as through tissue, may enable transgastric surgery.

In another variation, system 100 may include a second active cannula 102, which includes a second set of inner, middle, and outer drive modules connected to control computer 145. In this variation, the two active cannulas can be used as a parallel robot (a "Stuart Platform" is an exemplary type of parallel robot, but many variants are known in the art) whereby the tips of the inner flexible tubes of the two active cannulas are coupled to a single end effector 125. Doing so may enable the system to control the position and orientation of the end effector as well as control the stiffness of the position and orientation. In another application of the variation to system 100 having two active cannulas, the two active cannulas may be deployed within patient's anatomy 170 and used as retractors for holding soft tissue away from and exposing a surgical site.

Although the above description pertains to a surgical application of the present invention, it will be readily apparent to one skilled in the art that the present invention may be used in other applications that require guiding a device through a complex path that involves free space. Other applications may include manufacturing and micro-assembly, remote structural inspection, defusing ordinance, search and rescue within collapsed structures, and the like.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A surgical cannula, comprising: a first flexible tube having a first pre-formed curvature; a second flexible tube having a second pre-formed curvature, wherein the second flexible tube is disposed within the first flexible tube; a first actuator coupled to the first flexible tube, wherein the first actuator controls a translation and a rotation of the first flexible tube; and a second actuator coupled to the second flexible tube, wherein the second actuator controls a rotation and translation of the second flexible tube independently of the translation and rotation of the first flexible tube wherein said first and second flexible tubes store elastic energy in a configuration such that said elastic energy is releasable by translation of said second flexible tube relative to said first flexible tube and at least one of said first and second flexible tubes is configured to change shape as said second flexible tube is translated relative to said first flexible tube.

2. The surgical cannula of claim 1, wherein the first flexible tube is stiffer than the second flexible tube.

3. The surgical cannula of claim 1, wherein the first flexible tube has a first stiffness and the second flexible tube has a second stiffness, and
wherein the first stiffness and the second stiffness are substantially equal.

4. The surgical cannula of claim 1, wherein the first flexible tube comprises nitinol.

5. The surgical cannula of claim 1, wherein the first flexible tube has a straight portion.

6. The surgical cannula according to claim 1, wherein the first flexible tube comprises a region having a complex shape.

7. The surgical cannula according to claim 1, wherein the first flexible tube comprises a plurality of regions,
wherein for each of the plurality of regions the first flexible tube has a different thickness.

8. The surgical cannula of claim 1, wherein the second flexible tube comprises nitinol.

9. The surgical cannula of claim 1, wherein the second flexible tube has a straight portion.

10. The surgical cannula according to claim 1, wherein the second flexible tube comprises a region having a complex shape.

11. The surgical cannula according to claim 1, wherein the second flexible tube comprises a plurality of regions,
wherein for each of the plurality of regions the second flexible tube has a different thickness.

12. The surgical cannula of claim 1, further comprising a computer connected to the first actuator and the second actuator, wherein the computer comprises a computer readable medium encoded with a program for determining a shape of the surgical cannula based on a first flexible tube linear position; a first flexible tube angular orientation; the first pre-formed curvature; a second flexible tube linear position; a second flexible tube angular orientation; the second pre-formed curvature; and an overlap between the first flexible tube and the second flexible tube.

13. The surgical cannula of claim 1, further comprising:
a third flexible tube having a third pre-formed curvature, wherein the third flexible tube is disposed within the second flexible tube; and
a third actuator coupled to the third flexible tube.

14. The surgical cannula of claim 13, further comprising a computer connected to the first actuator, the second actuator, and the third actuator, the computer having a computer readable medium encoded with a program for determining a shape of the surgical cannula based on the a first flexible tube linear position; a first flexible tube angular orientation; the first pre-formed curvature; a second flexible tube linear position; a second flexible tube angular orientation; the second pre-formed curvature; a third flexible tube linear position; a third flexible tube angular orientation; the third pre-formed curvature; and an overlap between the first flexible tube, the second flexible tube, and the third flexible tube.

* * * * *